United States Patent
Rassman et al.

(10) Patent No.: US 6,882,420 B2
(45) Date of Patent: Apr. 19, 2005

(54) APPARATUS AND METHOD FOR IMAGING (75) Inventors: William Rassman, Los Angeles, CA (US); David Ralin, South Pasadena, CA (US); Robert A. Lieberman, Torrance, CA (US); Lothar U. Kempen, Redondo Beach, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 0 days.

(21) Appl. No.: 10/841,988

(22) Filed: May 7, 2004

(65) Prior Publication Data
US 2004/0207846 A1 Oct. 21, 2004

Related U.S. Application Data (63) Continuation of application No. 10/046,620, filed on Jan. 12, 2002, which is a continuation-in-part of application No. 09/838,700, filed on Apr. 19, 2001, and a continuation-in-part of application No. 09/614,503, filed on Jul. 11, 2000, now Pat. No. 6,594,011.

(51) Int. Cl.[7] .......................... G01J 4/00; G01N 33/557
(52) U.S. Cl. ...................... 356/369; 356/445; 436/517; 436/805
(58) Field of Search ............................ 356/364–369, 356/128, 136, 445, 446; 422/82.08, 11, 82; 435/6, 7.1, 288.7, 808; 436/517, 801, 527

(56) References Cited

U.S. PATENT DOCUMENTS

| | | |
|---|---|---|
| 4,238,565 A | 12/1980 | Hornby et al. |
| 4,256,834 A | 3/1981 | Zuk et al. |
| 4,508,832 A | 4/1985 | Carter et al. |
| 5,164,589 A | 11/1992 | Sjoedin |
| 5,229,833 A | * 7/1993 | Stewart .................. 356/364 |

(Continued)

FOREIGN PATENT DOCUMENTS

| | | |
|---|---|---|
| AU | 742417 | 2/2000 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

Tadashi Saitoh, et al. "Optical Characterization of Very Thin Hydrogenated Amorphous Silicon Films Using Spectroscopic Ellipsometry"; Japanese Journal of Applied Physics: vol. 30, No. 11B, Nov. 1991, pp. L1914–L1916.

"Handbook of Optics", Michael Bass Editor in Chief, by The Optical Society of America; vol. 1; pp. 4.23, 4.24; 1995 McGraw–Hill, Inc.

(Continued)

*Primary Examiner*—Hoa Q. Pham
(74) *Attorney, Agent, or Firm*—MacPherson Kwok Chen & Heid LLP; David S. Park

(57) ABSTRACT

Apparatus for acquiring an image of a specimen comprising a cassette having an optical portion holding a specimen array on a TIR surface and being removably matable to a processing portion having a polarized light beam source and a processing polarization-sensitive portion to image the spatially distributed charges in polarization of the specimen array. In one form the array optical portion comprises a transparent slide having a bottom surface with first and second gratings located to direct polarized light to the TIR surface and to direct light reflected by that (TIR) surface to an imager, respectively. The apparatus may include a flow cell integral with the optical portion as well as means for selecting the direction and wavelength of the polarized light.

23 Claims, 8 Drawing Sheets

U.S. PATENT DOCUMENTS

| | | | |
|---|---|---|---|
| 5,255,075 A | | 10/1993 | Cush |
| 5,313,264 A | * | 5/1994 | Ivarsson et al. ............. 356/73 |
| 5,437,840 A | | 8/1995 | King et al. |
| 5,483,346 A | | 1/1996 | Butzer |
| 5,485,277 A | | 1/1996 | Foster |
| 5,491,556 A | | 2/1996 | Stewart et al. |
| 5,573,956 A | | 11/1996 | Hanning |
| 5,593,130 A | | 1/1997 | Hansson et al. |
| 5,633,724 A | | 5/1997 | King et al. |
| 5,641,640 A | | 6/1997 | Hanning |
| RE35,716 E | | 1/1998 | Stapleton et al. |
| 5,753,518 A | | 5/1998 | Karlsson |
| 5,856,873 A | | 1/1999 | Naya et al. |
| 5,922,594 A | | 7/1999 | Loefas |
| 5,922,604 A | | 7/1999 | Stapleton et al. |
| 5,955,729 A | | 9/1999 | Nelson et al. |
| 5,965,456 A | | 10/1999 | Malmqvist et al. |
| 5,972,612 A | | 10/1999 | Malmqvist et al. |
| 6,008,010 A | | 12/1999 | Greenberger et al. |
| 6,008,893 A | | 12/1999 | Roos et al. |
| 6,045,996 A | | 4/2000 | Cronin et al. |
| 6,127,183 A | | 10/2000 | Ivarsson et al. |
| 6,140,044 A | | 10/2000 | Bessemer et al. |
| 6,143,513 A | | 11/2000 | Loefas |
| 6,143,574 A | | 11/2000 | Karlsson et al. |
| 6,197,595 B1 | | 3/2001 | Anderson et al. |
| 6,200,814 B1 | | 3/2001 | Malmqvist et al. |
| 6,207,381 B1 | | 3/2001 | Larsson et al. |
| 6,277,330 B1 | * | 8/2001 | Liu et al. ................. 422/82.05 |
| 6,289,286 B1 | | 9/2001 | Andersson et al. |
| 6,493,097 B1 | * | 12/2002 | Ivarsson ..................... 356/630 |
| 6,503,760 B1 | | 1/2003 | Malmqvist et al. |
| D472,644 S | | 4/2003 | Dawson et al. |
| 6,549,011 B1 | * | 4/2003 | Flatt .......................... 324/326 |
| 6,589,798 B1 | | 7/2003 | Loefas |
| 6,594,011 B1 | | 7/2003 | Kempen |
| D480,149 S | | 9/2003 | Dawson et al. |
| 6,698,454 B1 | | 3/2004 | Sjoelander et al. |
| 2002/0019019 A1 | | 2/2002 | Hamalainen et al. |
| 2002/0154311 A1 | | 10/2002 | Ivarsson |
| 2002/0182717 A1 | | 12/2002 | Karlsson |
| 2003/0022388 A1 | | 1/2003 | Roos et al. |
| 2003/0067612 A1 | | 4/2003 | Ivarsson |
| 2004/0002167 A1 | | 1/2004 | Andersson et al. |
| 2004/0012676 A1 | | 1/2004 | Weiner et al. |
| 2004/0023247 A1 | | 2/2004 | Xu et al. |
| 2004/0030504 A1 | | 2/2004 | Helt et al. |
| 2004/0038268 A1 | | 2/2004 | Pirrung et al. |

OTHER PUBLICATIONS

Bass, et al. "Handbook of Optics", by The Optical Society of America; vol. 1; Section 41.10; 1995 McGraw–Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930–2936, Aug. 1996.

Max Born et al. "Principles of Optics –Electromagnetic Theory of Propagation, Interference and Diffraction of Light", Sixth Edition, pp. 47–51 Pergamon Press.

Eggins, "Biosensors: An Introduction", pp. 112–113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3–4 pp. 439–449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7–D13, Papers No. 232–496 pp. 509–512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44–50, 1992.

Ulf Jonsson et al. "Flow–Injection Ellipsometry –An in Situ Method for the Study of Biomolecular Adsorption and Interaction at Solid Surfaces," Colloids and Surfaces, 13 (1985) pp. 333–339, 1985 Elsevier Science Publishers BV, Amsterdam, The Netherlands.

Jonsson, Ulf et al. "Biosensors Based on Surface Concentration Measuring Devices–The Concept of Surface Concentration" Progress in Colloid and Polymer Sci. vol. 70, pp. 96–100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10–11, 2000.

Harland G. Tompkins, et al. "Spectroscopic Ellipsometry and Reflectometry A User's Guide" A Wiley–Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381–1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139–146, 1994 Elsevier Science Publishers Ltd.

T.A. Ruzgas et al. "Ellipsometric Immunosensors for the Determination of γ–Interferon and Human Serum Albumin", Biosensors & Bioelectronics 7, pp. 305–308, 1992 Elsevier Science Publishers Ltd.

Haken Nygren et al. "Determination by Ellipsometry of the Affinity of Monoclonal Antibodies", Journal of Immunological Methods, 92, pp. 219–225, 1986 Elsevier Science Publishers Ltd.

John F. Place et al. "Opto–electronic Immunosensors: A Review of Optical Immunoassay At Continuous Surfaces", Biosensors 1, pp. 321–353, 1985 Elsevier Applied Science Publishers Ltd., England.

A. Brecht et al. "Biosensors: Fundamentals, Technologies and Applications" GBF Monographs, vol. 17, pp. 174–178, 1991 Germany.

Hakan Nygren et al. "Kinetics of Antibody–Binding to Surface–Immobilized Antigen: Influence of Mass Transport on the Enzyme–Linked Immunosorbent Assay (ELISA)", Journal of Colloid and Interface Science, vol. 107, No. 2 pp. 560–566, Oct. 1985 Academic Press, Inc.

Martin Malmsten et al. "Effects of Hydrophilization and Immobilization on the Interfacial Behavior of Immunoglobulins", Journal of Colloid and Interface Science 177, pp. 70–78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81–91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163–181, 1995 Humana Press Inc.

G. Elender et al. "Wetting and Dewetting of Si/SiO2–Wafers by Free and Lipid–Monolayer Covered Aqueous Solutions Under Controlled Humidity", Journal de Physique, II France 4 pp. 455–479, Mar. 1994.

C.F. Mandenius et al. "Coupling of Biomolecules to Silicon Surfaces for use in ellipsometry and other related techniques", Methods in Enzymology, vol. 137, pp. 389–394, 1988 Academic Press, Inc.

A.W. Flounders et al. "Patterning of immobilized antibody layers via photolithography and oxygen plasma exposure", Biosensors and Bioelectronics, vol. 12, No. 6, pp. 447–456, 1997 Elsevier Science Ltd., Great Britain.

A. Ahluwalia et al. "A comparative study of protein immobilization techniques for optical immunosensors", Biosensors and Bioelectronics 7, (1991) pp. 207–214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1–2.

Dr. Rudolf Oldenbourg, "A new view on polarization microscopy", Nature, vol. 381, pp. 811–812, Jun. 27,1996.

Clifford C. Hoyt et al. "Structural analysis with quantitative birefringence imaging", American Laboratory, pp. 34–42, Jul. 1999.

Dirk Honig et al. "Direct visualization of monolayers at the air–water interface by Brewster angle microscopy", J. Phys. Chem., pp. 4590 & 4592, 1991 American Chemical Society.

S. Henon et al. "Microscope at the Brewster angle: direct observation of first–order phase transitions in monolayers", Rev. Sci. Instrum. 62, (4) pp. 936–939, Apr. 1991 American Institute of Physics.

Gang Jin et al. "A biosensor concept based on imaging ellipsometry for visualization of biomolecular interactions", Analytical Biochemistry 232, pp. 69–72, 1995.

Pentti Tengvall et al. "Complement activation by 3–mercapto–1,2–propanediol immobilized on gold surfaces", Biomaterials vol. 17, No. 10 pp. 1001–1007, 1995 Elseviar Science Ltd., Great Britain.

H. Arwin "Spectroscopic ellipsometry and biology: recent developments and challenges", Thin Solid Films 313–314, pp. 7640774, 1998 Elsevier Science S.A.

Christopher Palmer "Diffraction Grating Handbook", pp. 35–44, 2000 Richardson Grating Laboratory, Rochester, New York.

* cited by examiner

APPARATUS AND METHOD FOR IMAGING

REFERENCE TO RELATED APPLICATIONS

This application is a continuation of U.S. application Ser. No. 10/046,620 filed Jan. 12, 2002, which is a continuation-in-part of U.S. application Ser. No. 09/838,700 filed on Apr. 19, 2001. U.S. application Ser. No. 10/046,620 filed Jan. 12, 2002 is also a continuation-in-part of U.S. application Ser. No. 09/614,503 filed Jul. 11, 2000 now U.S. Pat. No. 6,594,011. The contents of U.S. application Ser. No. 09/838,700 and U.S. application Ser. No. 09/614,503 are incorporated herein by reference.

FIELD OF THE INVENTION

This invention relates to imaging techniques and apparatus in conjunction with total internal reflection at the boundary of an optically transparent material and more particularly to the use of such techniques and apparatus for detecting the presence, composition, quantity, and spatial distribution of substances on optically transparent substrates.

SUMMARY OF THE INVENTION

This invention relates to imaging of a biochip (also referred to as a gene chip, protein chip, microarray and others) useful in applications, which, for example, utilize local polarization changes detected in the respective parts of the emerging light beam. U.S. Pat. No. 5,633,724 to King, et al. (1997) describes the readout of a biochemical array using the evanescent field. The King et al patent focuses on fluorescent assays, using the evanescent field to excite fluorescent markers attached to the substances to be detected and analyzed. The attachment of fluorescent markers or other molecular tags to the substances to be detected on the surface requires an additional step in performing the measurement, which is not required in the current invention. The King et al patent further describes use of a resonant cavity to provide an evanescent field for exciting analytes.

The formation of an array of biologically or chemically active spots on the surface of a substrate for identifying constituents in test material brought into contact with the array is well known. Typically, such processes require spots of, for example, oligonucleotides, DNA clones, antibodies, peptides, receptors, enzymes, inhibitors, etc. which are processed to exhibit fluorescence, electroluminescence, current change, voltage change—etc. for providing a detectable signature for the presence of constituents in the material being tested.

In accordance with the principles of this invention, light from a light source member providing an extended, polarized light beam, is directed through a transparent substrate and undergoes total internal reflection (TIR) at the surface of the substrate by a single reflection within the TIR member. Total Internal Reflection is described in: M. Born, and E. Wolf, "Principles of Optics", $6^{th}$ ed., pp 47–51, Pergamon Press, Oxford, 1991. The reflected light is detected by a polarization-sensitive, two-dimensional array detector or other type of detector. The changes of the local polarization state in the beam's cross-section caused by the total internal reflection are employed to obtain information about the presence and composition of substances in an array of substances on the substrate surface for each point of the surface. In accordance with one aspect of the invention, the light-generating element within the light source member is a quasi-monochromatic light source of moderate bandwidth.

In one embodiment, the light-generating element within the light source member is an Arc lamp. The light from the light source member is directed through an internal reflection member to reflect off a specimen. The total internal reflection at any point within the cross-section of the light beam causes a phase shift between the light component polarized in the plane of incidence and the component polarized perpendicular to the plane of incidence. The reflected light is detected by a polarization-sensitive detector such as a two dimensional array detector and the signal from this detector is then processed in a computer to provide two-dimensional information about substances on the surface of the specimen. Spatially distributed changes in polarization state in the cross-section of the reflected beam are indicative of the substances in the specimen in the location in the specimen array corresponding to a position in the detector. The apparatus and method is especially adapted for imaging material in an aqueous solution. It is furthermore particularly suited for detecting attachment and detachment of analytes to a two-dimensional biomolecular array positioned on the total internal reflection member as part of a molecular thin film system. In various applications a plurality of discrete specimen spots are presented in an array, where the method and apparatus will image the array so as to distinguish each of the discrete specimen spots. Fluorescence or molecular tagging is not necessary or practical for use in this invention.

Further, in accordance with the principles of this invention, the apparatus disclosed in the above-identified parent application provides an image of an entire array on a biochip or if desired a portion of the entire array.

In further embodiments the invention relates to a device having a removable portion, which in preferred embodiments is disposable or reusable, the removable portion defining a cassette having an optical element capable of receiving polarized light and directing it to a TIR surface to create an evanescent field in which the material to be imaged is positioned, and then upon a single reflection, reflecting the light beam to exit the optical element; the cassette also having a mounting structure to enable it to be mounted in the processing portion of the device that produces the polarized beam and receives it after reflection, for analysis. The cassette is designed to mount on the processing portion for operative interaction with the light beam as described herein. The cassette may be provided with a microarray of spots already in place on the optical element or it may be configured to receive a separate slide on which a microarray of spots have been placed. The cassette may be either disposable or reusable. When a separate slide is used in conjunction with the optical element, it is mounted on the optical element with an index matching fluid so that the surface of the slide on which the microarray is placed is the TIR surface.

In one aspect of the invention the optical element is a prism. A further specific aspect of the invention comprises the use of an optical element having gratings on it to control the direction of the incoming beam to enable TIR to occur instead of using a prism.

One of the goals is to define a cassette, which is sufficiently inexpensive that it is practical to dispose of it after a single use. While prisms can be used and reused, they are expensive. The aspect of the invention that uses gratings provides for a much less expensive cassette.

Nevertheless the use of gratings on an optical element to enable TIR to occur may be implemented broadly for any apparatus or method as an alternative to use of a prism. Also, certain other techniques are made available by use of gratings such as electronically alterable gratings and the use of holographic gratings.

DETAILED DESCRIPTION

The invention comprises a method and apparatus for analyzing a two-dimensional arrangement of chemical substances with an imaging technique. A polarized light source of known polarization state is directed into a total internal reflection member (TIR member) configured for a single reflection at a total internal reflection surface (TIR surface) and then exiting the TIR member. In the context of this document, superposition of reflections as encountered at a layered optical structure where the layer thicknesses are smaller than the coherence length of the illuminating light is referred to as a single reflection. The chemical specimen is in place above the TIR surface in the evanescent field of the reflected light beam. After reflection, the beam is passed to a polarization-sensitive two-dimensional detector such as a polarizer and a camera or other types of detectors. The beam's content can then be processed to determine the change in polarization state, locally in the two-dimensional cross-section of the beam. This provides a spatially distributed map of change of polarization state in the specimen. A variety of techniques are available to determine the change in polarization such as measuring the deviation from a null condition or by comparing the input polarization state to the output polarization state.

The refractive index composition of the materials within the evanescent field determines the change in the polarization state of the beam due to the reflection at the TIR surface. A two-dimensional variation of this composition within the TIR surface is associated with a respective variation of the polarization state spatially distributed across the cross-section of the reflected light beam.

In one application, the chemical specimen forms a two-dimensional array of molecules (here referred to as receptors) with specific affinities towards respective other molecules (here referred to as ligands). In this application, the invention is utilized to indicate the presence or absence or rate of binding between ligands and receptors on the array. Such arrays commonly consist of a plurality of discrete specimen spots. The present method and apparatus images the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the TIR surface in the evanescent field. Described in more detail below are different embodiments of the invention.

Figure 1:
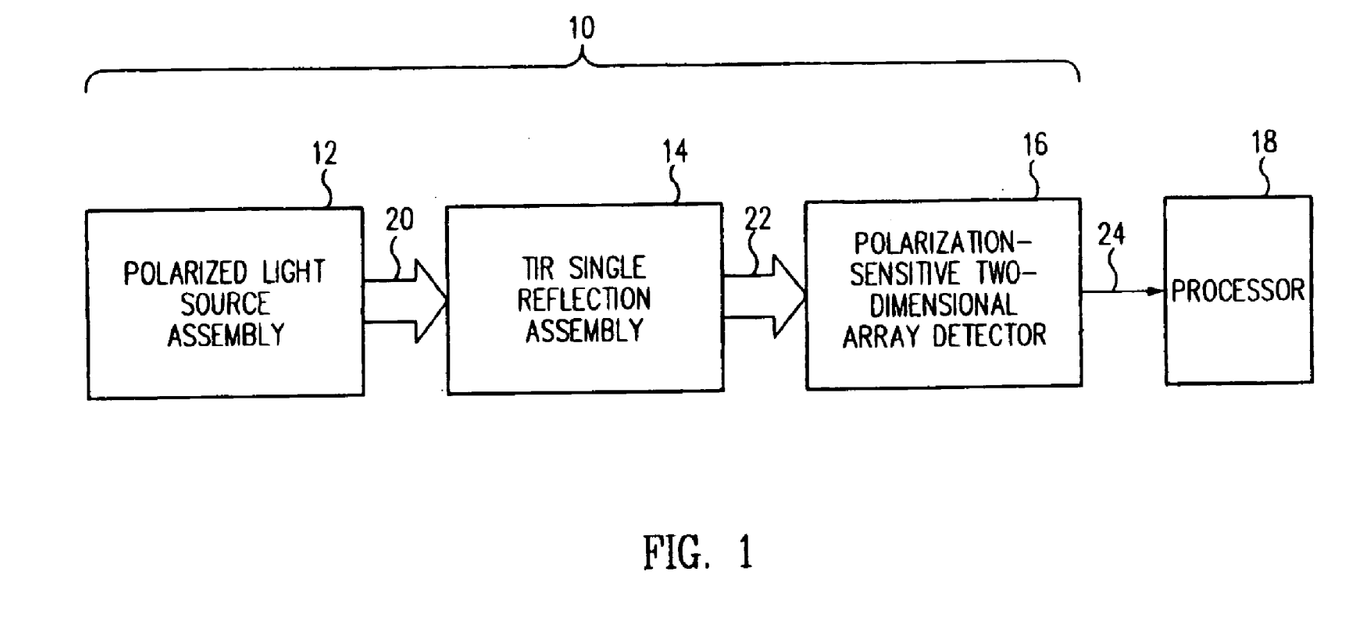
FIG. 1 is a block diagram of an illustrative system in accordance with the principles of this invention.
Figure 2:
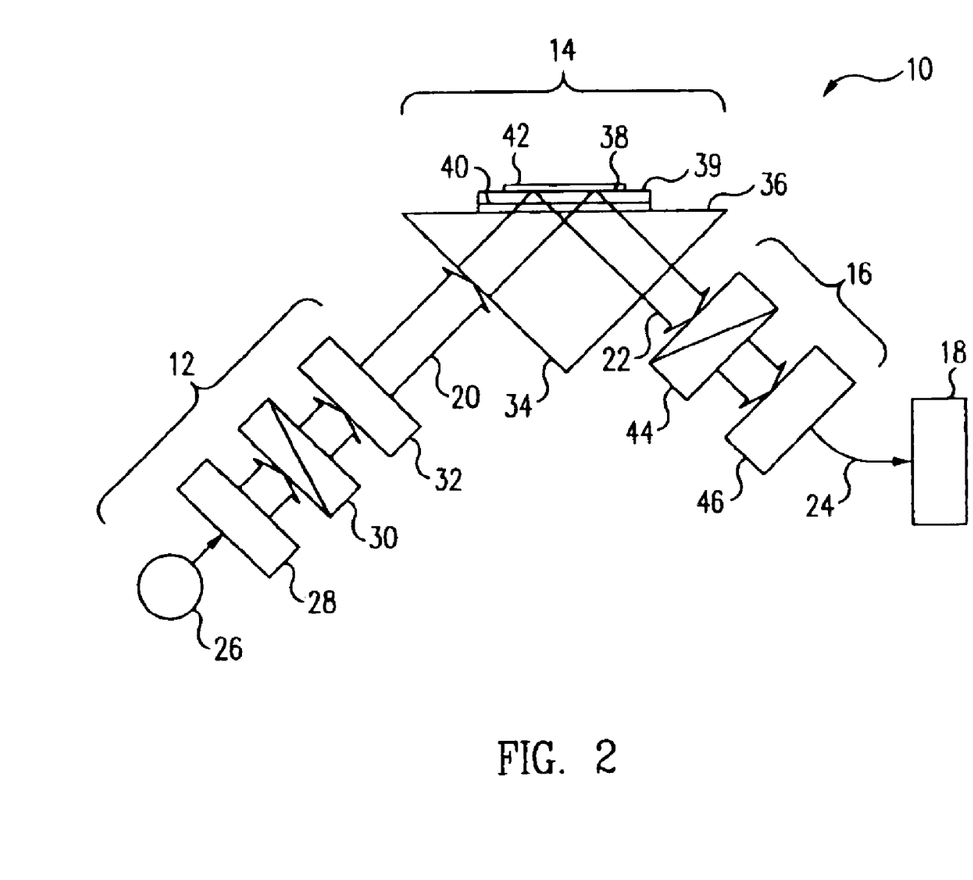
FIG. 2 is a block diagram of an embodiment of the system of FIG. 1.

FIGS. 1 and 2 show an apparatus, which implements one embodiment of the invention. As shown in FIG. 1, the apparatus 10 can be described conveniently as consisting of three general portions. Portion 12 is a polarized light source assembly, portion 14 is a total internal reflection assembly providing a single reflection and portion 16 is a polarization-sensitive imaging detector assembly which can employ for example a two-dimensional array detector. Data from the detector assembly 16 is sent by an electrical signal 24 to processor 18 such as a specially programmed computer and user access system such as a print-out or image display. Data can be presented as an image, a data table, graph or in other forms. The polarized light source assembly 12 passes polarized light of known polarization state, (which may be varied or varying) 20 to the total internal reflection assembly 14 where a single reflection occurs and the reflected light 22, having a changed polarization state passes to the detector assembly 16, where it is recorded spatially over the cross-section of the beam. The recorded data are sent to the processor 18 where the change of polarization state, is determined to provide a spatially resolved map of changes in polarization state. Where the specimens are presented as an array of discrete spots, each spot will be imaged for its change in polarization state within the spot area.

FIG. 2 shows a more detailed schematic block diagram of the preferred embodiment. The polarized light source assembly 12 has a light source 26, a beam forming member 28 (if the nature of the light source is such as to make beam forming useful or necessary) a polarizer 30 and an optical retarder 32. The total internal light reflection assembly 14 has an optical element 34 which has an optical surface 36. Also shown is a specimen slide 38 on the optical surface 36, and between them an index matching substance 40. Because substance 40 is index matched a total internal reflection surface (TIR surface) is defined as the upper surface 39 of the specimen slide 38. A specimen 42 is positioned on the total internal reflection surface 39 of the slide 38. In one embodiment of the invention, the optical element 34 is a prism configured along with the index-matched slide 38 in relationship to the incoming light beam 20, and the exiting light beam 22 such that the beam reflects only a single time at the TIR surface 39 and then exits the prism. If the specimen is placed directly on the optical surface 36, then the optical surface 36 would be the TIR surface. But this is not the usual application, since the specimen (such as a biochip) is usually prepared more conveniently on a specimen slide 38 and placed in the apparatus. However constructed, the invention, incorporates an optical structure having a TIR surface and the beam reflects only a single time at the TIR surface between entering and leaving the optical structure. In other words, there is a TIR surface in optical contact with the specimen, such that the evanescent field associated with the total internal reflection interacts with the specimen, and there is only a single reflection at that TIR surface.

The post reflection detector assembly 16 has a polarizer 44, and an imaging detector, for example a two-dimensional array detector 46, preferably a camera of the CCD or CMOS array type. The processor 18 is a specially programmed computer (or processor) and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector.

The processor 18 receives the data as an electrical signal (on connector 24) and characterizes the change of polarization state spatially over the two-dimensional array. In the processor 18, the analysis and processing is done in one embodiment by comparing the known polarization state of the incoming light from the light processing assembly 12 with the changed polarization state of the reflected light 22, spatially resolved two-dimensionally within the beam which provides a map of spatially distributed points or spots in the specimen array. The polarization shift is then analyzed by the processor 18 to provide information of the presence and properties of elements in the chemical specimen. Other known techniques, such as null processing can be used to determine the change in polarization state.

Alternatively, the light source member 26 may be an LED, an SLD (Super Luminescent Diode), an incandescent light source, or a laser. If an LED or SLD is used, the set-up shown in FIG. 2 is appropriate, where the beam-forming member 28 is a collimator. If an incandescent light source is used, an optical filter is also used. In one embodiment, the light source 26 for the apparatus is a quasi-monochromatic light source of moderate bandwidth. In accordance with the invention the light source 26 is preferably an LED of moderate bandwidth. Preferably the bandwidth is a full width half maximum wavelength in the range of about 10 nm–50 nm, and more preferably a full width half maximum wavelength in the range of about 30 nm–50 nm.

In an alternative embodiment, the optical retarder 32 as shown in FIG. 2, could be placed instead in the exiting beam path 16 at the location 22 before the polarizer 44.

Figure 3:
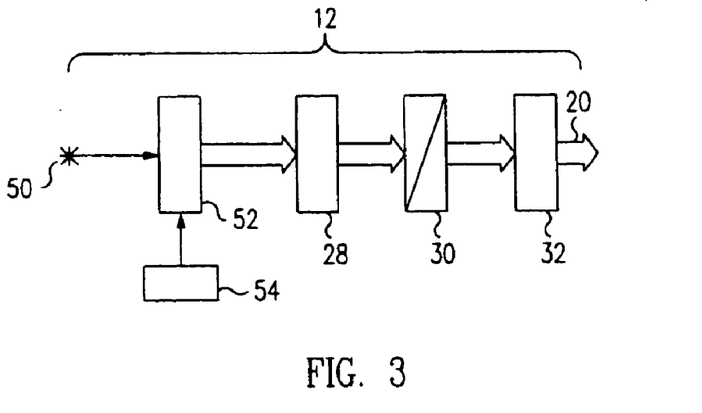
FIGS. 3, 4 and 5 are block diagrams of alternative portions of the system of FIG. 1.

FIG. 3 shows an additional embodiment. In embodiments in which the light source is a laser 50, a moving diff-user 52 is adapted to produce speckle-offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The beam 20 then proceeds through the beam-forming element 28, the polarizer 30 and the optical retarder 32, exiting the light source assembly 12 at the location 20.

The polarizer 30, in embodiments as shown in FIGS. 2 and 3, employs a polarizer of selected known polarization state. The polarizer 30 may be of the type having a mechanical actuator driven by a motor control signal so as to enable the variation and selection of the polarization state of the light beam 20.

As mentioned above, the total internal reflection optical element 34 (of FIG. 2) either alone or in combination with an index matched slide may be arranged for use with a specimen in various ways to define a total internal reflection assembly so long as the specimen is in the evanescent field of the reflected beam 20,22.

As noted above, the specimen 42 (of FIG. 2) could be set directly on the optical surface 36 in which case the optical surface 36 would be the TIR surface. But this is inconvenient and repeated use is likely to degrade the optical quality of the optical surface 36. Therefore, consistent with common practice in which a biochip or other chemical assay specimen is provided, a specimen slide 38 or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a slide 38, being index matched so that there is a TIR surface 39.

Figure 4:
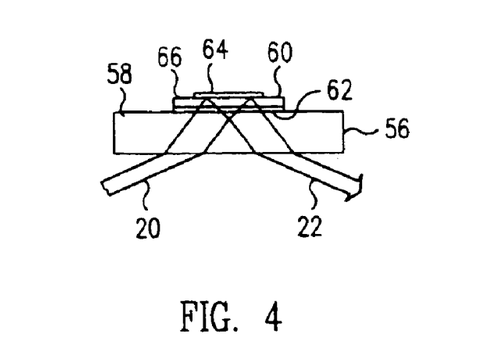
Figure 5:
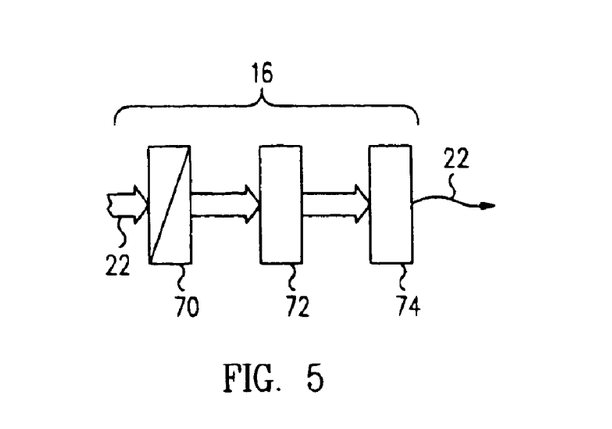

FIG. 4 shows an alternative optical arrangement in which a flat optical member 56 having an upper surface 58 is surmounted by a specimen slide 60 with an index matching substance 62 on which is a specimen 64 is mounted. The TIR surface 66 is the top of the slide 60. The beam 20 enters the assembly, is refracted as it enters, and leaves the optical member 56 after a single reflection at the TIR surface 66 as beam 22. Other mechanisms for providing total internal reflection and an evanescent field can be employed in practicing this invention as long as only a single reflection occurs at the TIR surface upon which the specimen is placed so as to be in the evanescent field associated with the reflection. As seen in FIG. 5, the post-reflection processing arrangement 16 through which the beam 22 passes, can alternatively, consist of a polarizer member 70, a beam forming member 72 and an imaging detector 74 such as a two dimensional array detector or other type of imaging detector.

The method and apparatus can be used in combination with biochips of the type having discrete specimen spots or a micro-titer plate containing an array of discrete spots or locations for analysis, where the detected change in polarization state is spatially related to the discrete locations in the reflected beam. Therefore, as used herein the slide and specimen refers to any type of chemical or biological array that is desired to be examined.

The foregoing described apparatus and methods are especially beneficial for imaging materials in an aqueous medium.

The invention as described above provides an extremely sensitive optical imaging system for real-time imaging of the binding status of biochip array elements on the surface of an optically transparent material such as a glass or plastic chip. An exemplary monitored array a 15 mm square inscribed in the 20 mm circular field, with discrete specimen spots of size commensurate with the lateral resolution of the imaging optics resulting in fully parallel, continuous real-time read-out of up to 5 million sensor fields. Sensor sensitivity to surface attachment is in the femtogram/mm$^2$ range (e.g. one DNA per square micron).

The apparatus of FIG. 1 operates by imaging the pattern of reactions on the biochip. Those reactions produce changes in the height, surface concentration, or refractive index of the material that reacts at each spot. The area imaged could be the entire biochip array or a portion of the entire biochip array. By providing an array of spots of different materials, different constituents in test material flowed over the spots bind in a manner which identifies those constituents. By including in a computer memory the positions of the various materials in the different spots of the array, the image produced by the apparatus of FIG. 1 not only identifies the constituents in the test material, but also can determine the rate at which the reactions occur. With the apparatus described, height differences can be imaged dynamically over such short periods of time that intermediate height change readings can be recorded and therefore height change rates can be determined as well as allowing comparison of the rate of height change or intermediate amount of height change among the spots on the biochip array.

A process using the apparatus and a biochip is as follows:

Place the biochip surface in a flow cell in combination with the apparatus such that the surface of the slide which has the spots is the TIR surface; initially calibrate the apparatus, such that light reflected from the biochip yields a fully-linear polarization; and adjust the analyzer to a null position to fully block the linearly polarized light.

When the null position is achieved, every region where the chip (slide) surface deviates from the initial state stands out as a bright spot the intensity of which is directly related to the thickness (height) differences induced by the deviation. A solution containing target molecules are flowed over the biochip surface. The intensity changes caused by changes in the polarization of the light reflected by the biochip may be monitored continuously across the array to study thickness changes that occur on the biochip. The relative intensity measured at the detector is related to the sample parameters and the setting of the polarizing elements using computer programs based on a detailed "Jones calculus" sensor system description. With these programs, theoretical plots are fitted to the acquired measurement data sets, and the outputs' dependence on parameter variations can be visualized. At the start of the procedure, the apparatus is adjusted so that the image of the entire biochip is homogeneously dark. As the target molecules begin to bind to the reference probes the intensity of the images of the spots increases. The intensity is expected to be the highest for high affinity interactions and mild changes are expected for low affinity interactions. The rate of intensity change can be related to the affinity constraints of the system. For example, using a properly prepared biochip, in a single procedure, the affinity measurements for multiple peptides can be performed. Moreover, the effect of binding density (because different concentrations of peptides are used in spotting) can also be measured.

Although reference is made to biochips in the example, the procedure and the results apply generally to chemically sensitive materials on a TIR surface.

The invention has been described above in terms of a prism having a TIR surface, and having on the surface an array of molecular spots. In another embodiment, also described above the array is formed on a separate slide positioned on the prism with index matching fluid between them so that only the upper surface of the slide forms the TIR surface.

In another aspect of the invention referred to as the cassette embodiment, the invention is configured such that the portion on which the micro array spots are placed (also called the specimen array) is a partially or wholly disposable cassette or a reusable cassette.

In embodiments where the cassette is a separate or separable structure, the assembly elements, which include the light source and its related elements and the elements that receive, record and analyze the light after it has been reflected in the specimen cassette, is in aggregate defined herein as the processing assembly.

A basic exemplary separate cassette of this type comprises an optical assembly which may be simply an optical element that produces the evanescent field and the single TIR including, as an integral part, the surface that contains the microarray (the specimen). The cassette also includes a mount or frame portion in which the optical assembly is held. The mount or frame portion is configured along with mating configuration in the processing assembly to fit operatively in the processing assembly. This cassette assembly can be manufactured and provided to users who have available the other portion of the device, the processing assembly, that being the portion that provides the light source and light processing elements before the polarized light beam enters the optical assembly of the cassette as well as the portions that process the light after it exits the optical assembly of the cassette. The two assemblies, the cassette and the processing assembly are constructed so that the cassette is fitable to the processing assembly in such a way that they function cooperatively as described above. Also, the cassette can be constructed to include or receive a flow cell either manufactured as an integral part of the cassette or configured to mate to the cassette optionally, as desired. The cassette can be made to be reusable or disposable while the processing assembly comprises a permanent device available to users who will obtain and use the cassettes as needed.

Such an embodiment of the invention is directed at providing a wholly or partially disposable or reusable cassette in which the optical element and the mount or frame portion define a cassette. The cassette in its most basic configuration has an optical element or optical assembly that has a surface on which a specimen array has been placed, that surface defining the TIR surface. The optical element or optical assembly also has an optical transmission portion, which directs the extended beam of polarized light from the processing assembly to the TIR surface to create an evanescent field by a single reflection of the beam, and then directs the beam out of the optical transmission portion back into the processing assembly. The frame or mount portion allows the optical element or optical assembly to be carried safely and to be easily and accurately installed for use in the processing assembly.

Alternatively, the specimen array can be provided on a separate slide placed on the optical element, preferably with index matching fluid, so that the upper surface of the slide will be the TIR surface. The other assembly, the processing assembly has a receiving and locating portion that is matingly configured with the configuration of the frame or mount portion of the specimen cassette such that the cassette will fit in sufficiently precise orientation in or on the processing assembly. Orientation of the cassette with the processing assembly is important in order to ensure that the polarized light from the processing assembly will be properly directed to reflect a single time at the TIR surface and produce an evanescent field encompassing a single one, a sequence of areas, or all of the desired areas of the specimen array on the TIR surface. In other words, the cassette is oriented such that evanescent effects occur on the TIR surface upon which the desired specimens lie. The reflected light then exits the specimen cassette to be received by a reflected light-analyzing portion of the processing assembly. The light analyzing portion determines the change in polarization spatially in the evanescent field to give a two dimensional image.

In a configuration of the processing assembly in which the polarized light source section and the reflected light analyzing section are not adjustable, more precise orientation of the cassette with the processing assembly is required in order that the incoming beam be directed as desired at the TIR surface and the outgoing beam be redirected to the analyzing section. In particular, the specimen array is placed on the TIR surface in the evanescent field. However, in a configuration in which either or both of the light source section and the analyzing section are adjustable, a number of advantages are available. One advantage is that orientation of the cassette need only be sufficiently precise to be within the range of adjustability of those adjustable sections. Other advantages of adjustability address the variable size and arrangement of the specimen array or sub-arrays on the TIR surface, the adjustability allowing proper direction and focusing of the light beam where the specimen array(s) are in different locations or arrays cover different areas or for selection of sub-arrays to be analyzed separately.

The adjustability allows proper direction and focusing of the light beam for single reflection and placement of the evanescent field where varying size and arrangement of specimen arrays and sub-arrays are in different locations, where arrays cover different areas and where selection of imaging sub-arrays is desired. In addition to or as an alternative to making the processing assembly adjustable, this adjustability can be build into the cassette, so as to place a desired portion of the specimen array or sub-arrays within the path of the light beam for a single TIR at the TIR surface.

Figure 6:
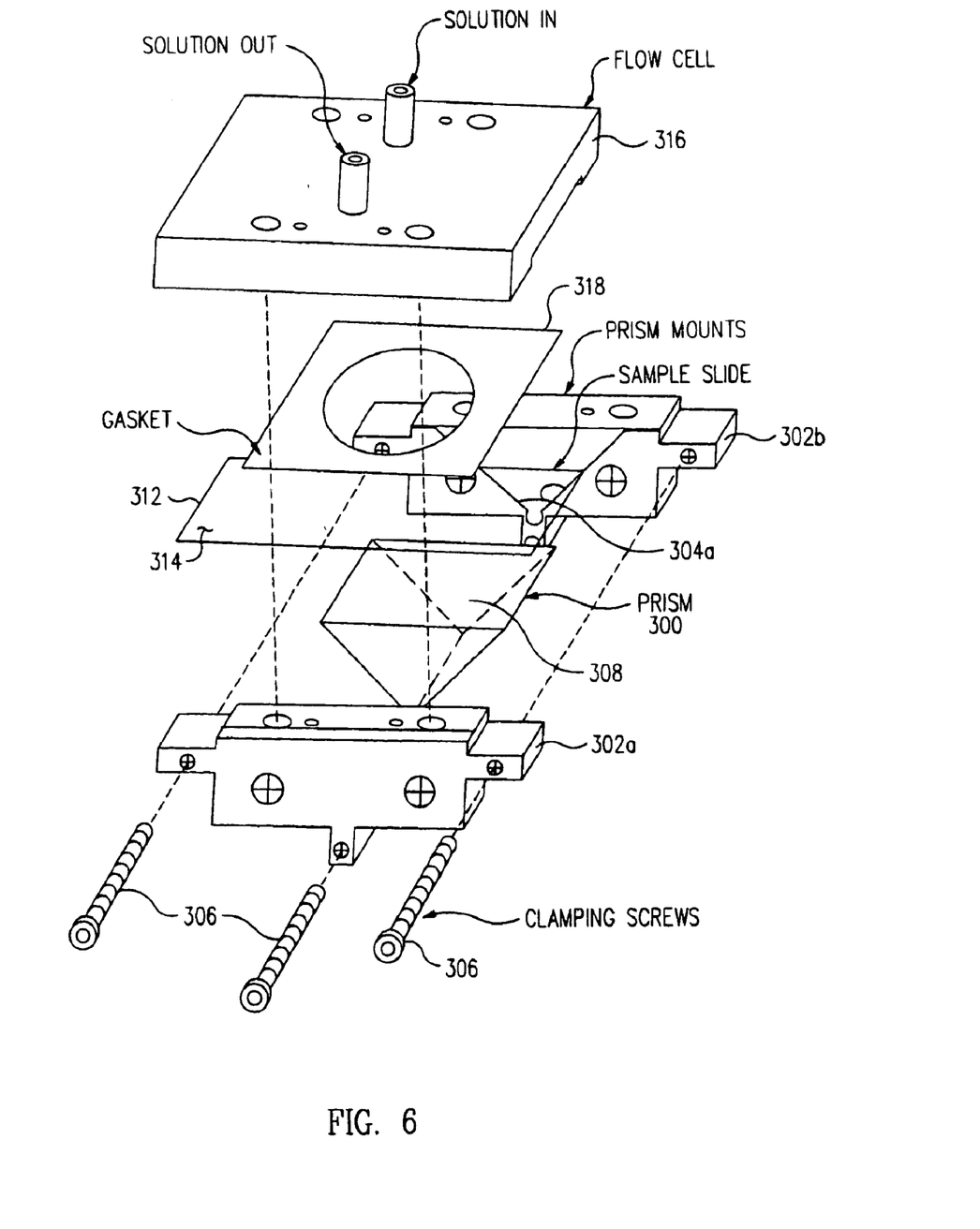
FIG. 6 is an exploded view of a combined optical assembly and a flow cell.

An exemplary configuration of a cassette is shown in FIG. 6 in which a prism 300 is held in prism mounts 302a and 302b by way of the retaining surfaces 304a and 304b formed into the inside faces of the prism mounts 302a and 302b respectively (not shown). Therefore, when the prism mounts 302a and 302b are secured together as with screws 306 with the prism 300 between them, the prism is locked in place. In this configuration the prism 300 and the prism mounts 302a and 302b define a basic cassette when the specimen-array spots are placed on the surface 308 which is the top surface of the prism. and operates as the TIR surface. The prism mounts 302a and 302b are configured to be received in the processing assembly in the proper orientation for use. In this configuration as least the prism 308 is disposable or reusable after using the microarray of spots that have been positioned on its top surface 308. Alternatively, a sample slide 312 can be used as a carrier for the micro array spots by being placed on top of the prism surface 308 with an index matching fluid between them so that the top surface 314 is the TIR surface. In this configuration only the slide 312 would have to be disposable. Subject to cost considerations, the entire cassette could be disposable. In any case the cassette can be reusable with a new biochip or even a reclaimed biochip.

Alternatively, when desired the cassette can be defined by the addition as shown in FIG. 6 of a flow cell 316 along with a gasket 318.

In a further embodiment, the slide itself can provide a TIR surface in the absence of a prism as described hereinbefore. In effect, the slide can serve the purpose of the prism, which is directing the light to and from the TIR surface at a proper angle to cause total internal reflection as well as providing the TIR surface. But in this embodiment, the bottom surface of the slide includes a grating operative on light entering the slide at an appropriate angle to create the requisite TIR conditions for the evanescent field above the TIR surface, with an array of localized polarization changes due to the change to specimen array spots, to be imaged in a single reflection at the TIR surface.

Figure 7:
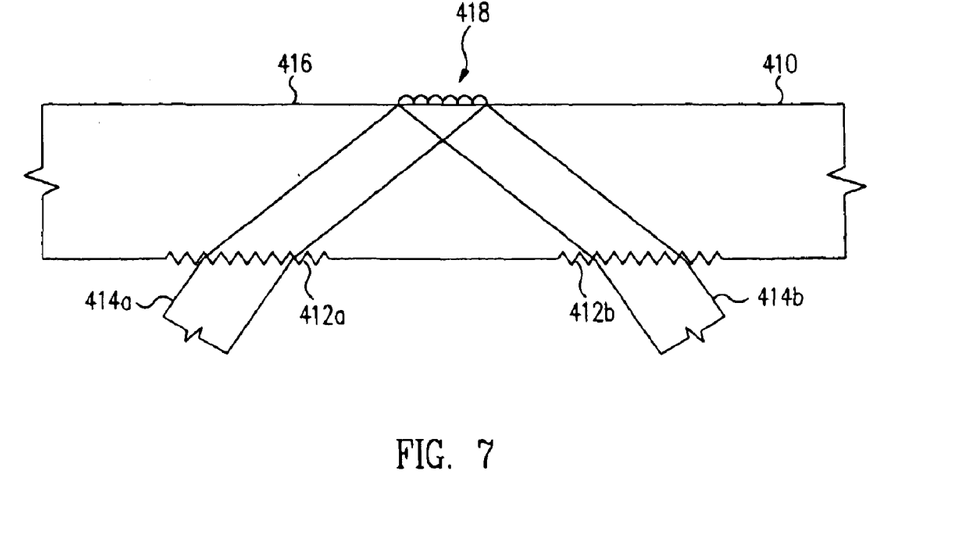
FIG. 7 is a schematic side view of an alternative optical element.

FIG. 7 shows schematically a slide 410 with gratings 412a and 412b formed on its bottom surface (as viewed). The gratings are placed so as to intercept the incoming light beam 414a and outgoing light beam 414b respectively, to provide the correct angle for a single TIR at the surface 416 on which a specimen array 418 is placed. It is clear that a slide with a grating on its bottom surface (as viewed) serves the purpose of a prism (directing the light at the correct angle) as well as providing an inexpensive and disposable slide on which specimen array may be formed for imaging. With the optical element therefore being defined as a slide with appropriate gratings as described to achieve a single TIR a very inexpensive fully disposable cassette can be configured.

It is to be understood that gratings are operative to direct polarized light in a manner consistent with the TIR, single reflection conditions to receive the reflected light in a polarization sensitive detector so that by resolving changes in polarization spatially over a two dimensional area, the area can be imaged in accordance with the principles of this invention.

Figure 9:
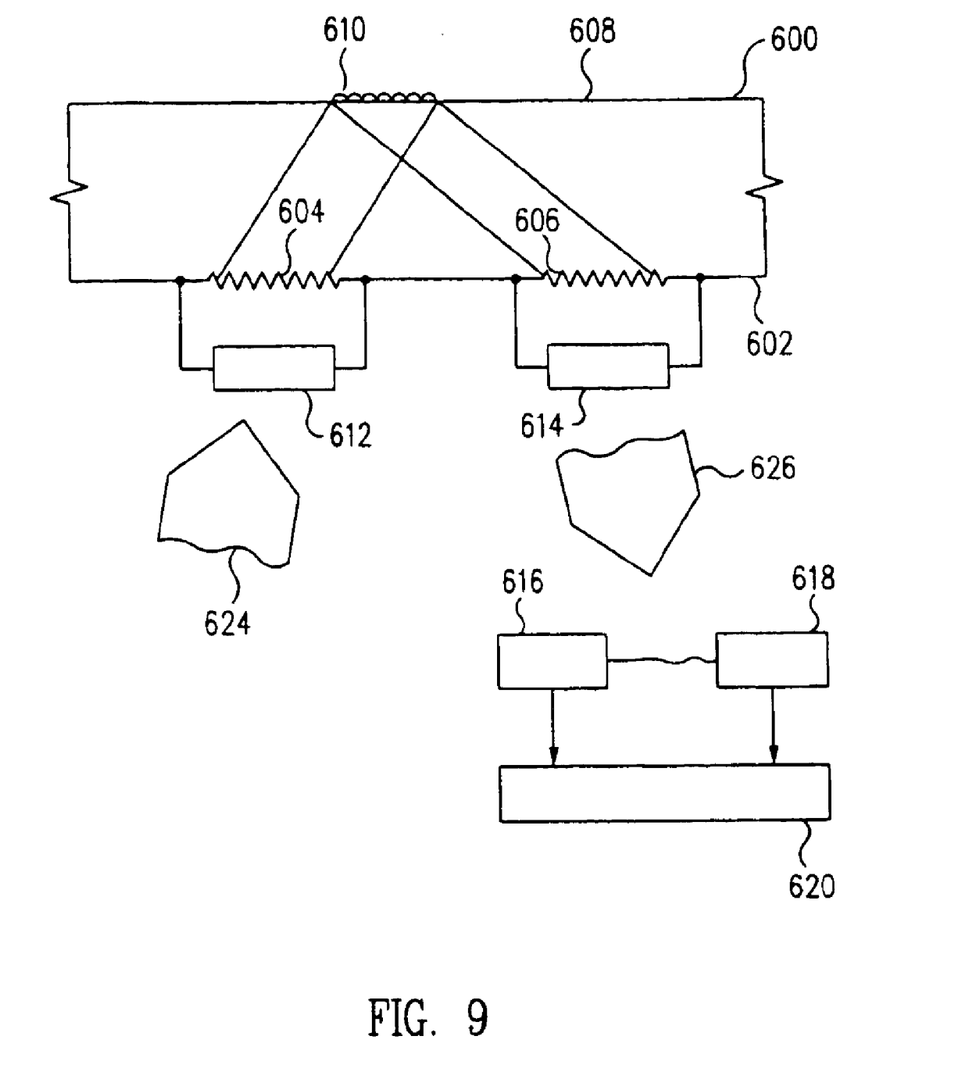
FIG. 9 is a schematic block diagram of an alternative optical assembly.

However the use of gratings as described, to divert light from total internal reflection, is not limited to the single reflection concept as described above, but can be employed in any case which a TRI surface and an evanescent field are desired. These include for example applications where a plurality of reflection occur and in cases using surface plasmon resonance structures Gratings may be either of the surface-relief type or of the refractive index type, and may be fixed or electrically controllable. Fixed surface-relief gratings, and methods for their fabrication, are well understood, and are described in Born and Wolf (op cit.), pp401–418. Electrically controllable surface-relief gratings include surface acoustic wave (SAW) devices. Refractive index gratings, sometimes referred to as Bragg gratings, consist of periodic variations in refractive index, and may be either fixed or, when fabricated in electooptically active materials, electrically controllable. Acousto-optic effects can also be used to create electrically tunable refractive index gratings (Handbook of Optics, op cit., Vol. 2, Chapter 12). Bragg refractive index gratings and methods for their fabrication in optical fibers are discussed in G. Meltz, et al. Optics Lett., 14, p823, 1989. Fabrication of Bragg gratings in other glass materials, such as slide 410 in FIG. 13 or optical member 600 in FIG. 15 can be accomplished using similar means.

An electrically alterable grating allows for the control of the depth of penetration of the evanescent field into the specimen array. That is, the height of the evanescent field above the TIR surface can be controlled. This control over the depth of penetration also can be accomplished by a mechanism to permit the movement of the light source along an arcuate path to change the direction of the light input or by the use of a filter at the light source to change the wavelength of the input light. Control over the depth of penetration of the evanescent field permits the acquisition of real time data representative of the changes in height and/or mass of molecular bindings at the various sites of the specimen array by successive output images with varying depth of penetration of the evanescent field.

In embodiments, in accordance with the principles of this invention, it may be desired to employ light of differing wavelengths for examining receptor ligand interactions. Techniques for permitting control over the use of differing wavelengths include the use of a filter wheel and/or the changing of the angle at which light is directed from the light source. The use of a dielectric stack filter with collimated light also permits the elimination of light at all wavelengths except a selected wavelength. The inclusion of more than a single imager also is useful in embodiments employing such techniques. These techniques also allow for wavelength selection choices, which avoid any noise, which may be present in the system.

Figure 8:
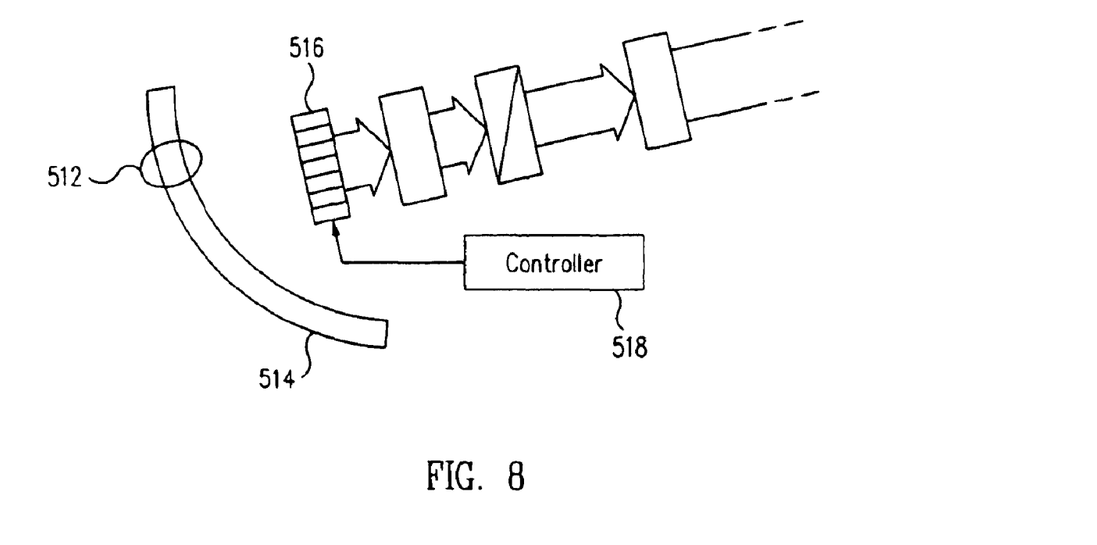
FIG. 8 is a schematic block diagram of an alternative light source arrangement.

FIG. 8 schematically illustrates an embodiment in which a polarized light source 512 is mounted on a mechanism (not shown) for repositioning the light source along an arcuate path indicated by curve 514. Further, the light from source 512 is directed through a filter wheel 516. Filter wheel 516 and the position of the light source along curve 514 are controlled by controller 518 for selecting the depth of penetration of the evanescent field (i.e. its height over the TIR surface). The above depth control techniques may be used separately or in concert.

FIG. 9 also shows an optical member 600 for a use in a cassette having a lower surface 602 on which gratings 604 and 606 have been placed. The TIR surface 608 contains a microarray 610. Also, shown are grating biasing field sources 612 and 614 for altering the spacing in gratings 604 and 606 if electrically alterable gratings are formed on the slide surface 602. The figure also shows a plurality of imagers 616, 618, such as CCD memories; such imagers are located in different positions for capturing (input) light directed at (1) different angles along curve 514 of FIG. 8 or (2) at different angles imposed by the gratings. The output of any of the images are applied to a computer 620 for analysis. Therefore polarized light 624 enters the optical member 600 passing through the gratings 604 and then, after reflection at the TIR surface 608, light 626 passes through the gratings 606.

Figure 10A:
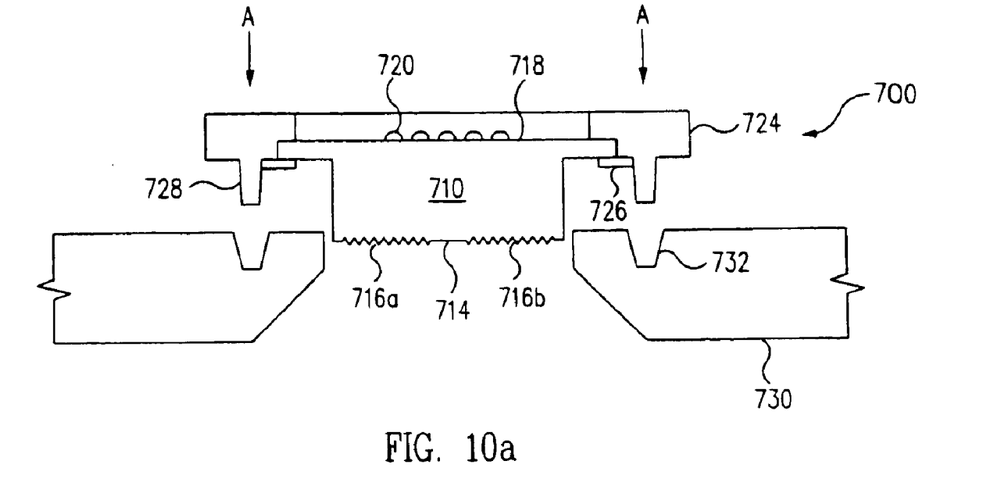
FIG. 10a is a schematic side view of a specimen cassette ready for positioning in the processing assembly.
Figure 10B:
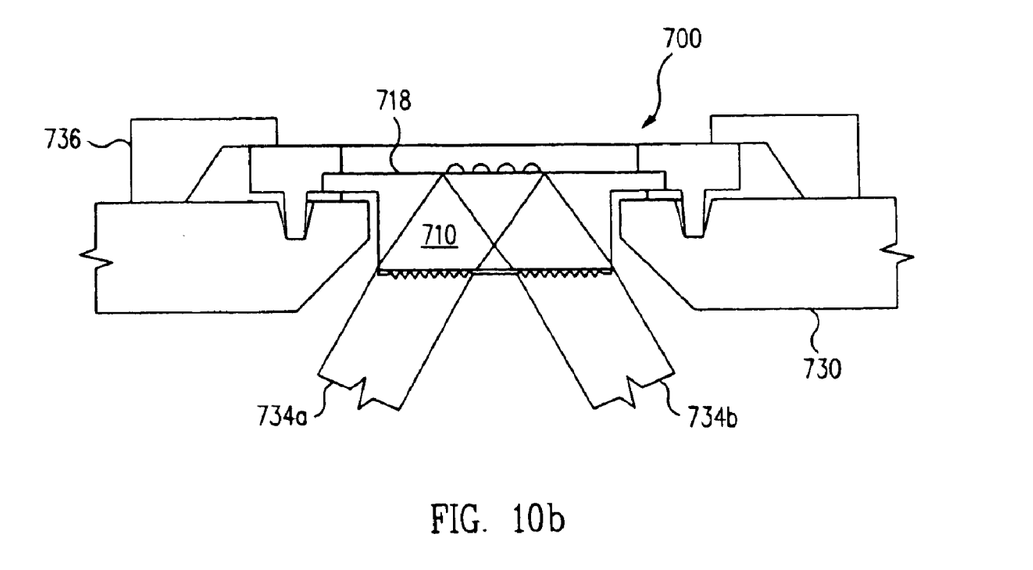
FIG. 10b is a schematic side view of a specimen cassette positioned in the processing assembly.

FIGS. 10a and 10b show a representative cassette 700 in which the optical element has gratings for directing the light beam. Specifically, FIG. 10a shows an optical element 710 having a lower surface 714 on which gratings 716a and 716b have been placed. It has an upper surface 718 on which the specimen array 720 resides. The cassette 700 has a frame or mounting portion 724 and a retaining collar 726 to receive and retain the optical element 710 in the cassette 700. The frame or mounting portion 724 has pins 728. Also shown is a portion of the processing assembly 730 having receptacles 732 for receiving the pins 728, when the cassette 700 is lowered into place as indicated by arrows A—A. Thus, as seen in FIG. 16b when the cassette is in place, the light beam 734a and 734b can enter and exit respectively the optical element 710 properly for TIR at the surface 718. Clamps 736 hold the cassette 700 in place in the processing assembly 730.

Figure 11A:
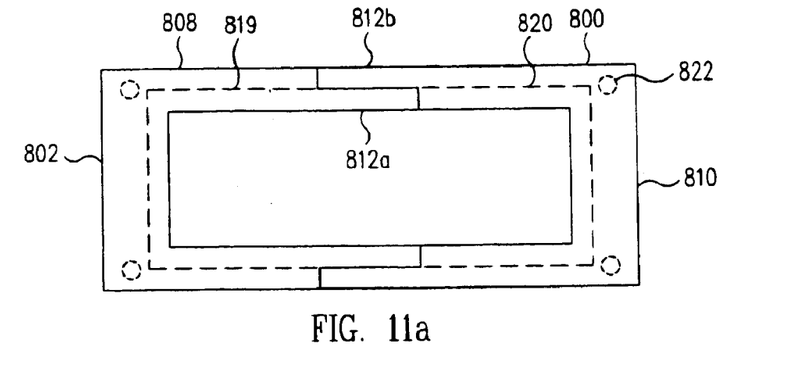
FIGS. 11a, 11b, 11c, and 11d are schematic views of a slide and slide holder for an embodiment of the system.
Figure 11B:
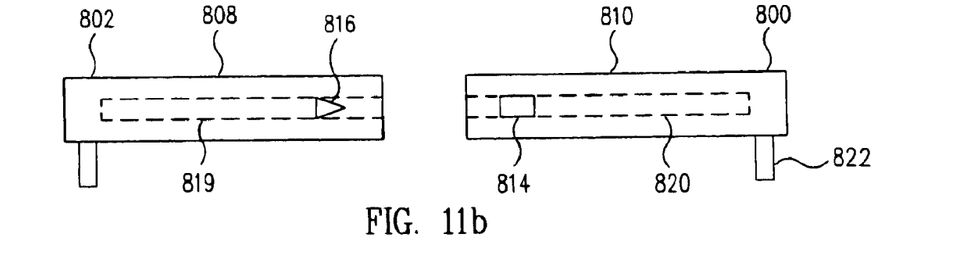
Figure 11C:
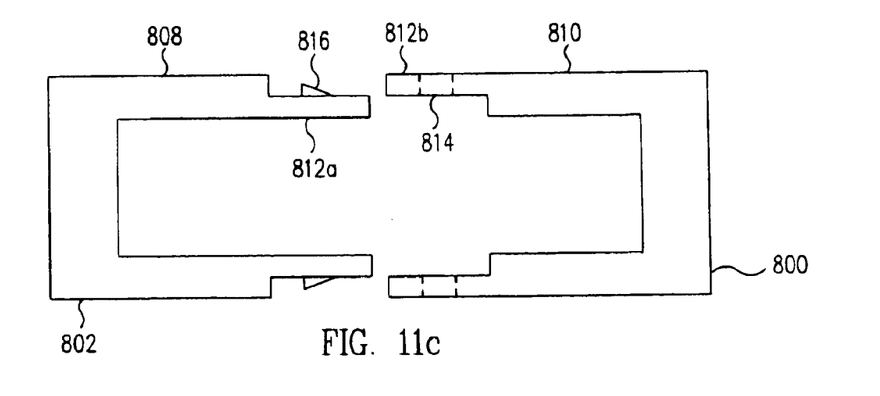
Figure 11D:
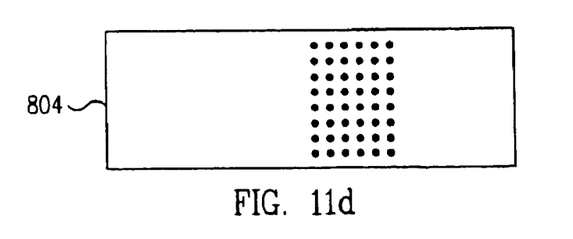

Another exemplary configuration is cassette 800 using a slide as shown in FIGS. 11a through 11d. That configuration comprises a frame 802 and an optical member 804 on which a specimen array 806 is applied as shown in FIG. 11d. The frame 802 has a first side 808 and a second side 810, each of which has a mating connection portion 812a and 812b in this case on opposite legs of the sides 808 and 810 respectively. In this configuration the connection portions 812a and 812b comprise an aperture 814 on one leg and a detent 816 on the other leg. The frames sides 808 and 810 have recessed shelves 819 and 820 that match when the two parts are assembled. The recessed shelves 819 and 820 are sized to retain the optical member slide 804 that is configured to fit into the shelves. The frame has a minimum of two posts 822 extending downwardly, four posts being preferred. The posts fit into mating receptacles in the processing assembly for locating the specimen assembly with the processing assembly. This cassette 800 can be used in conjunction with a prism, or as an independent slide, or the lower surface of the slide 804 can be fitted with gratings as described above. Certainly numerous configurations can be devised to construct a cassette having an optical member, a TIR surface on which a specimen array is placed and a mount, the cassette being configured to fit in or on the processing assembly to function as described herein.

An important process available with the devices described above is dynamic imaging, that is in addition to recording an image at the end of a procedure such as a binding experiment run with a flow cell over a microarray, images can be captured and processed intermittently between the start and the end so that intermediate status and time progression of the binding experiment can be analyzed.

What has been described herein is merely illustrative of the principles of this invention. It is well within the purview of those skilled in the art to design various, modifications of the invention within the spirit and scope of the following claims. For example, it may be advantageous to image a single portion of an array of interactions on a slide or to scan a succession of such portions. Further, it may be advantageous to aperture the image directed at the imager to obtain scattering cross sections. Such expedients relate to applications of the apparatus herein.

What is claimed is:

1. A cassette for use with an imaging apparatus, said cassette comprising:

an optical element comprising a reflective surface to allow formation thereon of a specimen array, the optical element being configured to direct a polarized light beam from a light source to the reflective surface, such that a reflection of the polarized light beam at the reflective surface generates an evanescent field in the vicinity of the specimen array; and a mount or frame coupled to the optical element and having a locating portion engageable with a mating locating element of a two-dimensional array detector adapted for providing an image based on spatially distributed polarization changes in the light beam.

2. The cassette of claim 1, wherein the optical element includes a prism.

3. The cassette of claim 2, wherein the optical element includes a transparent slide operably coupled to the prism.

4. The cassette of claim 1, wherein the cassette and the light source are configured for a single reflection of the light beam at the reflective surface.

5. The cassette of claim 1, wherein the mount or frame is operable to locate at least a selected portion of the specimen array in the evanescent field.

6. The cassette of claim 1, wherein the reflective surface comprises the upper surface of a transparent slide, the slide having a lower surface, the lower surface comprising at least one grating and the upper surface including an array of receptors thereon.

7. The cassette of claim 6, wherein the at least one grating comprises a first grating positioned to intercept the polarized light beam from the light source and a second grating positioned to intercept the light beam after it has reflected from the upper surface.

8. The cassette of claim 6, wherein the at least one grating comprises an electrically alterable grating.

9. The cassette of claim 6, wherein the at least one grating comprises a Bragg grating.

10. The cassette of claim 6, wherein the at least one grating comprises an electrically alterable hologram.

11. The cassette of claim 1, further comprising a flow cell secured to the reflective surface, the flow cell including an inlet port and an outlet port for flowing analyte across the specimen array.

12. A cassette for use with an imaging apparatus, said cassette comprising:

an optical element including a prism and a slide having a reflective surface to allow formation thereon of a specimen array, the optical element being configured to direct a polarized light beam from a light source to the reflective surface, such that a reflection of the polarized light beam at the reflective surface generates an evanescent field in the vicinity of the specimen array; and a mount or frame coupled to the optical element and having a locating portion engageable with a mating locating element of a two-dimensional array detector adapted for providing an image based on spatially distributed polarization changes in the light beam, the mount or frame being operable to locate at least a selected portion of the specimen array in the evanescent field.

13. The cassette of claim 12, wherein the cassette and the light source are configured for a single reflection of the light beam at the reflective surface.

14. A cassette for use with an imaging apparatus, said cassette comprising:

an optical element comprising a reflective surface to allow formation thereon of a specimen array, said optical element being configured to direct a polarized light beam from a light source to the reflective surface, such that a reflection of the polarized light beam at the reflective surface generates an evanescent field in the vicinity of the specimen array; and a mount or frame coupled to the optical element and having a locating portion engageable with a mating locating element of a processing assembly.

15. The cassette of claim 14, wherein the processing assembly includes a two-dimensional array detector adapted for providing an image based on spatially distributed polarization changes in the light beam.

16. The cassette of claim 14, wherein the processing assembly includes the light source.

17. The cassette of claim 14, wherein the mount or frame is operable to locate at least a selected portion of the specimen array in the evanescent field.

18. The cassette of claim 14, wherein the reflective surface comprises the upper surface of a slide, the slide having a lower surface, the lower surface comprising at least one grating and the upper surface including an array of receptors thereon.

19. The cassette of claim 18, wherein the at least one grating comprises a first grating positioned to intercept the polarized light beam from the light source and a second grating positioned to intercept the light beam after it has reflected from the upper surface.

20. The cassette of claim 18, wherein the at least one grating comprises an electrically alterable grating.

21. The cassette of claim 18, wherein the at least one grating comprises a Bragg grating.

22. The cassette of claim 18, wherein the at least one grating comprises an electrically alterable hologram.

23. The cassette of claim 14, further comprising a flow cell secured to the reflective surface, the flow cell including an inlet port and an outlet port for flowing analyte across the specimen array.

* * * * *